United States Patent [19]
Steinböck et al.

[11] Patent Number: 5,474,276
[45] Date of Patent: Dec. 12, 1995

[54] VALVE FOR CONTROL OF A BRANCH LINE

[75] Inventors: Wolf-Dietrich Steinböck, Graz; Günther Pucher, Hengsberg; Horst Rüther, Gritsch; Helmut Zach, Graz, all of Austria

[73] Assignee: AVL Medical Instruments AG, Schaffhausen, Switzerland

[21] Appl. No.: 285,424

[22] Filed: Aug. 4, 1994

[30] Foreign Application Priority Data

Aug. 5, 1993 [AT] Austria .................................... 1565/93

[51] Int. Cl.$^6$ ....................................................... F16K 7/06
[52] U.S. Cl. .................... 251/4; 251/7; 137/883
[58] Field of Search ............................ 251/4, 7; 137/863, 137/883

[56] References Cited

U.S. PATENT DOCUMENTS 2,674,435  4/1954  Angell ........................................... 251/7
3,874,850  4/1975  Sorensen et al. .
4,428,745  1/1984  Williams ................................... 251/4 X
4,484,599  11/1984  Hanover et al. ........................ 251/4 X

FOREIGN PATENT DOCUMENTS 391214  10/1960  Austria .

Primary Examiner—John C. Fox
Attorney, Agent, or Firm—Watson, Cole, Grindle & Watson

[57] ABSTRACT

In order to avoid dead volumes in a valve for control of a branch line departing from the main line in a valve chamber located in a valve housing, the valve chamber contains an elastomer part provided with a main channel and a branch channel departing from it, and the two ends of the main channel are sealingly connected with the main lines. The free end of the branch channel is sealingly connected with the branch line, and further that a valve lifter be provided in the valve housing, which acts on the branch channel in the branch-off area directly adjacent to the main channel of the elastomer part, thus reducing the cross-section of the branch channel, which is held in place by a counterpiece in the valve housing.

10 Claims, 3 Drawing Sheets

VALVE FOR CONTROL OF A BRANCH LINE

BACKGROUND OF THE INVENTION

The invention relates to a valve for control of a branch line departing from a main line in a valve chamber located in a valve housing, and to a valve block for selection of different measuring modules of an analyzing apparatus with several such valves.

Analyzers, in particular for analyzing samples of body fluids, which are provided with containers for calibrating and washing solutions as well as one or more feed openings for entering individual samples or sample series, usually have a large number of valves for control of the sample, calibrating and cleansing media.

DESCRIPTION OF THE PRIOR ART

In Austrian Patent 391 214, for example, an analyzing apparatus is described which permits simultaneous measurement of several clinically relevant measuring parameters by means of a single analyzer, i.e., with the use of series-connected measuring modules. Otherwise, such parameters would have to be determined by a number of separate devices.

Another such analyzing apparatus is disclosed in U.S. Pat. No. 3,874,850. This apparatus is provided with measuring modules for determination of the pH value, the $CO_2$ and $O_2$ concentrations, and the analysis of hemoglobin.

For especially valves for the control of a branch line which departs from or opens into a main line, it is essential that practically no residual volumes of the sample fluid or calibrating or washing liquid be left in the passage from the main line to the seal in,the branch line. If fluid remnants remained in the branch lines leading towards the measuring modules, for example, these residues would dry up in the course of a subsequent drying process, and would contaminate the medium passing through afterwards, thus obscuring measured results.

SUMMARY OF THE INVENTION

It is an object of the invention to propose a valve for control of a branch line departing from or opening into a main line, in which the branch-off in the fully functional valve be essentially free of dead volumes. In addition, a valve block comprising several such valves is proposed.

In the invention this object is achieved by providing that an elastomer part be placed in the valve chamber, which is provided with a main channel and a branch channel departing therefrom, and that the two ends of the main channel be sealingly connected with the main line, and that the free end of the branch channel be sealingly connected with the branch line, and further that a valve lifter be provided in the valve housing, which acts on the branch channel in the area of the branch-off directly adjacent to the main channel of the elastomer part, thus reducing the cross-section of the branch channel which is held in place by a counterpiece in the valve housing. The use of the above valve permits branch lines to be sealed in close proximity to the main line, so that only a negligibly small dead volume will remain between the main line and the sealing site in the branch line, which may be rinsed and dried easily during the washing and drying phase.

In further development of the invention it is provided that the elastomer part be T-shaped and have toroidal rings at its three ends, which are placed in corresponding grooves in the valve housing. In the T-shaped elastomer part the main channel has an interior diameter of 1 mm, for example, and the branch channel an interior diameter of 0.6 mm. By means of the valve lifter actuated by the valve drive the branch channel of the elastomer part is squeezed shut in the immediate vicinity of the main channel, and a seal is formed in this way. In the closed state a minute wedge-shaped dead space is formed next to the main channel, which may be rinsed and dried easily.

To prevent the volume of the elastomer part displaced upon squeezing from narrowing the main channel, a clearance space is provided for the elastomer part in the valve chamber. When the branch channel is squeezed shut, the main channel can give way by assuming a curved shape. The curved passage has no negative effects on the washing and drying operation.

The invention further provides that the main channel and branch channel be configured as capillary tubes each projecting into one of the three ends of the elastomer part and being sealed by it.

A valve block of the invention for selection of different measuring modules of an analyzing apparatus with two or more valves is characterized in that the valves are located in a joint valve housing, and that the branch lines of the individual valves depart from a common main line and are connected to the measuring modules of the analyzing apparatus via fittings at the valve block.

In known analyzers as aforedescribed the individual measuring modules with electrodes for blood gases (BG), ions (ISE), etc., are arranged one behind the other. The disadvantage of this arrangement is that in the course of a selective measurement of ISE parameters, for instance, all measuring modules are contaminated by the sample one after the other, and all measuring modules have to be washed, dried and newly conditioned upon completion of the measuring process. Another drawback of series-connected measuring modules is that the calibrating media must be compatible with all types of sensors used.

The valve block described by the invention will permit individual selection of the individual measuring modules as required, thus avoiding the above drawbacks. If for clinically relevant reasons only one group of parameters is to be analyzed, for example, the other measuring modules will remain unaffected, which will reduce the consumption of test chemicals and measuring time. Other advantages are that the measuring modules may be individually charged with optimally adapted reagents for cleaning, conditioning and calibrating operations.

Manufacture of the valve block is greatly simplified by providing the valve housing in two parts, i.e., an upper part for the elastomer components and the main and branch lines, and a lower part for the valve lifters and, if required, a valve drive. The upper part may be made of plexiglass, and the lower part of aluminum, for instance.

As the individual measuring modules in blood gas analyzers are maintained at a constant temperature of 37° C., it will be of advantage if the lower part of the valve housing is also maintained at this temperature. In this way the sample and all other operating media will enter the measuring modules at a temperature of 37° C., and temperature-induced signal distortions are avoided.

In this context it will be of further advantage if the valve block is provided with a heat exchanger allocated to the main line for the purpose of heating sample and operating media.

BRIEF DESCRIPTION OF THE DRAWINGS

The invention will now be further described with reference to the accompanying drawings, in which.

DETAILED DESCRIPTION OF THE PREFERRED EMBODIMENT

Figure 1:
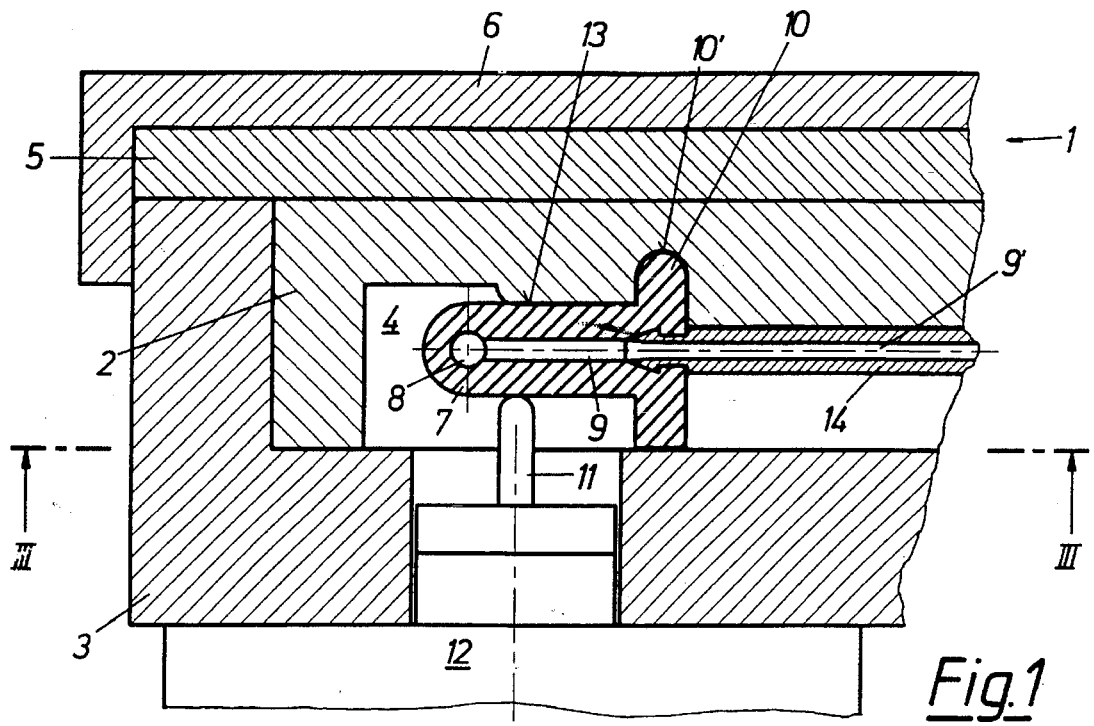
FIG. 1 shows a section of a valve of the invention.
Figure 2:
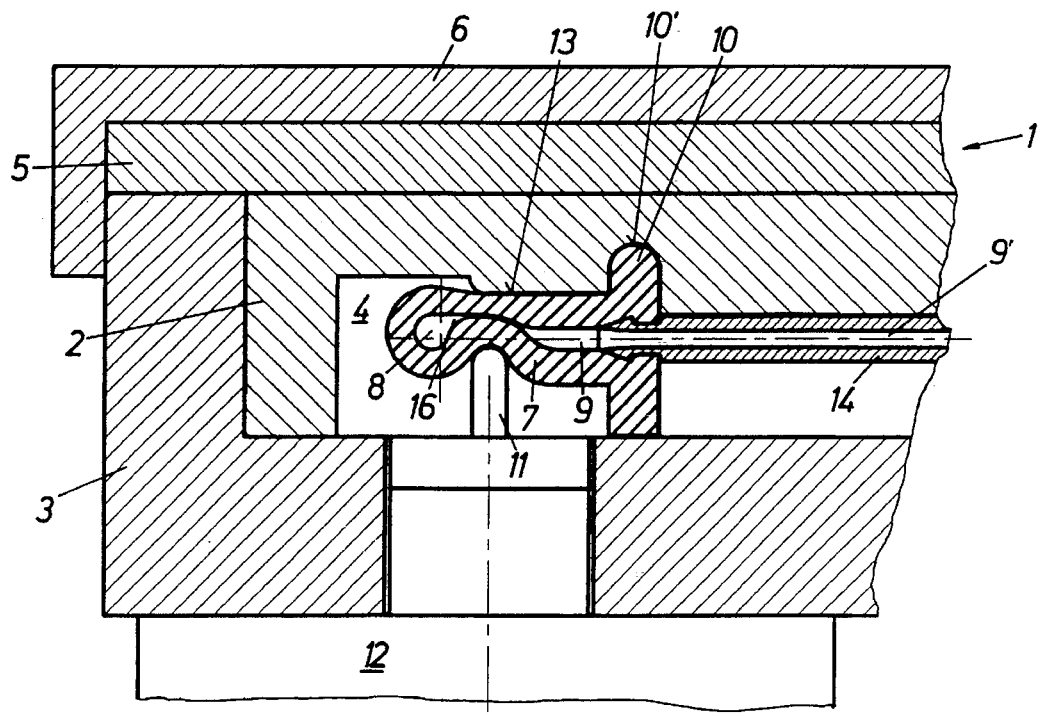
FIG. 2 shows the valve in FIG. 1 with the branch channel closed or squeezed shut.
Figure 3:
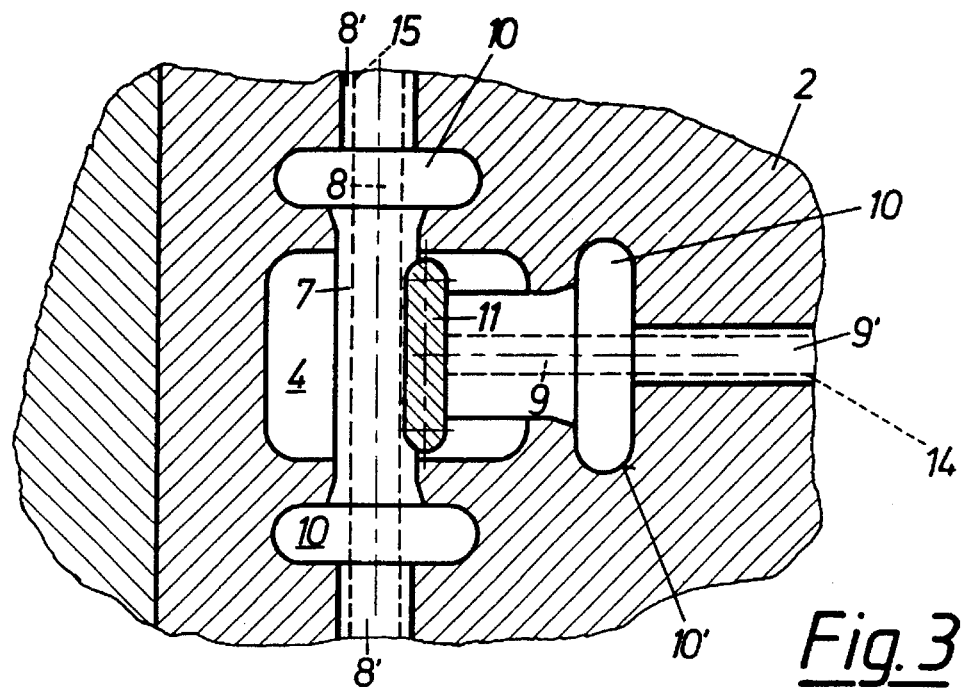
FIG. 3 shows a section of the valve in FIG. 1 along line III—III thereof.
Figure 4:
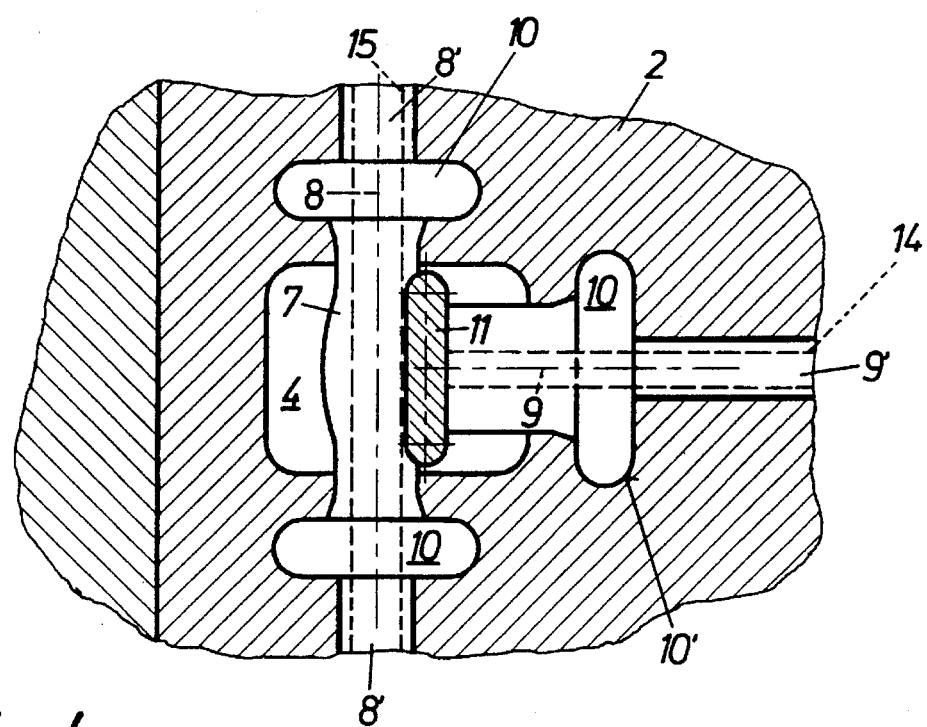
FIG. 4 shows the valve in FIG. 3 with the branch channel closed.

The valve shown in FIGS. 1 to 4 in different sections and operating states is provided with a valve housing 1 comprising an upper part 2 and a lower part 3, the two parts enclosing a valve chamber 4. In addition, FIGS. 1 and 2 show a cover plate 5 and its fastening element 6.

In the valve chamber 4 an elastomer part 7 is located which is provided with a main channel 8 and a branch channel 9 departing therefrom. The two ends of the main channel 8, which are configured as toroidal rings 10, are sealingly connected with the main line 8' in the upper part 2 of the valve housing 1. The free end of the branch channel 9, which also is configured as a toroidal ring 10, is sealingly connected with the branch line 9' in the upper part 2. The toroidal rings 10 of the T-shaped elastomer part 7 may be placed in suitable recesses or grooves 10' in the upper part 2 of the valve housing 1.

The valve housing 1 further contains a valve lifter 11, which is actuated by a valve drive 12 and acts upon the branch channel 9 in the branch-off area directly adjacent to the main channel 8 of the elastomer part 7 so as to reduce the cross-section of the branch channel 9, the latter being held in place by a counterpiece 13 in the valve housing 1.

The main line 8' and the branch line 9' may be configured as capillary tubes 14, 15, each projecting into one of the three end pieces of the elastomer part 7 acting as seals. The elastomer part 7 is shown with its branch channel 9 open in FIGS. 1 and 3, and with its branch channel 9 squeezed shut in FIGS. 2 and 4. As is clearly shown in FIG. 2, only a negligibly small wedge-shaped dead space 16 next to the main channel 8 will remain in the closed state, which may be rinsed and dried easily. It is furthermore shown, in particular in FIG. 4, that enough clearance space is provided for the elastomer part 7 inside the valve chamber 4, permitting the main channel 8 to give way by assuming a curved shape when the branch channel 9 is squeezed shut.

Figure 5:
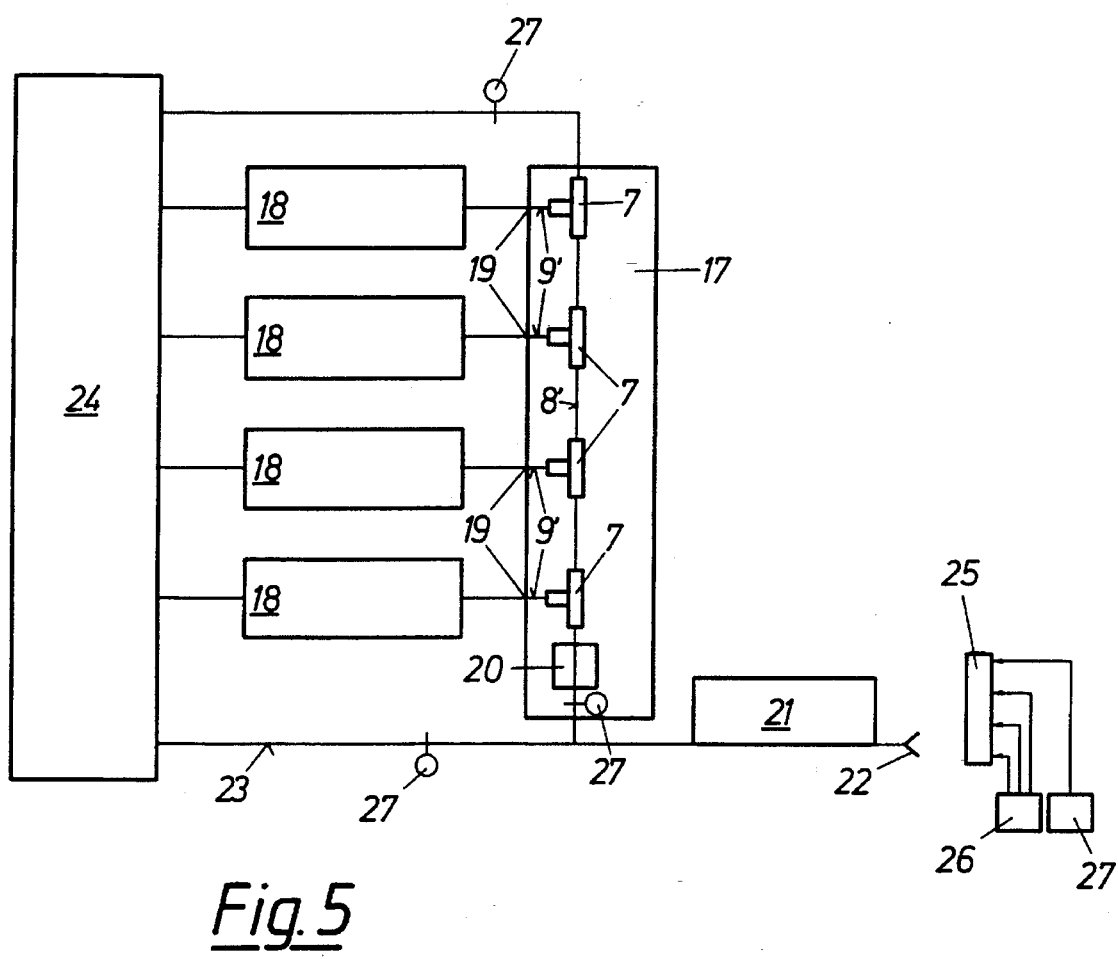
FIG. 5 shows a valve block of the invention as part of an analyzing apparatus.

FIG. 5 shows a valve block 17 which is integrated in an analyzing apparatus represented only schematically, and which has several valves as illustrated in FIGS. 1 to 4 with an elastomer part 7 each. By means of the individual valves of the valve block 17 the units of the battery of measuring modules 18 of the analyzer may be selected individually. The branch lines 9' of the individual valves depart from a common main line 8' and are connected with the measuring modules 18 of the analyzer via fittings 19 at the valve block 17.

The lower part 3 of the valve housing 1 may be made of a material with good thermal conductivity, such as aluminum, whereas the upper part 2 may be made of plexiglass. To heat the sample and the operating medium, the valve block 17 may be provided with a heat exchanger 20, which is allocated to, or is in thermal contact with the main line 8'. With the use of the aluminum part of the housing and the heat exchanger 20 the sample and the calibrating media may be maintained at a constant temperature of 37° C. As a consequence, a sample storage chamber 21 located in front of the valve block 17 need not be temperature-controlled. Another advantage is that a temperature control is provided for a defined sample volume, regardless of the actual sample volume filled into the feeder funnel 22. Any excess amount of sample fluid may be drained via a tube 23 into the waste container of a pump block 24.

The individual measuring modules 18 may be used for the following analyses:

ISE analysis, i.e., the analysis of ions by means of ion-sensitive electrodes (ISE electrodes). Ions such as sodium, potassium, chloride, calcium, lithium, and magnesium are analyzed in this process.

BG analysis, i.e., the analysis if the blood gas parameters $pO_2$, $pCO_2$, and pH.

The measuring process takes place as following. The sample is entered via the feeder funnel 22 into the sample storage chamber 21, where tube 23 serves as an overflow. With the use of a docking disk 25 as described in Patent 391 214 mentioned above, washing and calibrating media are delivered to the feeder funnel 22 via feeder passages bearing the collective reference number 26. Controlled by optical sensors not shown in this drawing, and with the use of squeezed tube valves 27 at the input and output end of the valve block 17 as well as in tube 23, the sample and any washing and calibrating media used are delivered to the thermostat-controlled measuring modules 18 by means of a peristaltic pump not shown in the pump block 24. The heat exchanger 20 located in the valve block 17 is used to heat the sample to the temperature required for the measuring modules.

When the measuring modules 18 have been charged with the sample the measuring signals are recorded and stored in the system's processor not shown here. During the subsequent washing phase the entire sample path from the feeder funnel 22 to the measuring modules 18 employed is washed and dried.

After the sample has been washed out calibration is initiated; the calibrating solution is sucked into the measuring modules 18 via the docking disk 25, and the signals from the measuring modules 18 are recorded. The signals delivered by the measuring modules for the sample and the calibrating media are used to compute the measurement results which are then displayed to the user. This marks the end of the measuring process and the apparatus will be ready for a new measuring cycle.

We claim:

1. Valve for control of a branch line extending from a main line in a valve chamber located in a valve housing, wherein an elastomer part is provided with a main channel and a branch channel extending therefrom, said main channel and said branch channel lying in a common plane, opposing ends of said main channel being sealingly connected with said main line, and a free end of said branch channel being sealingly connected with said branch line, a valve lifter provided in said valve housing, said branch channel bearing against a counterpiece in said valve housing, said valve lifter acting on said branch channel toward said counterpiece in a direction perpendicular to said plane and in an area directly adjacent said main channel of said elastomer part for reducing the size of said branch channel.

2. Valve according to claim 1, wherein said elastomer part is T-shaped, toroidal rings provided at said opposing ends and said free end, said rings being located in corresponding grooves provided in said valve housing.

3. Valve according to claim 2, wherein said main line and said branch line are configured as capillary tubes, each said tubes projecting into said opposing ends and said free end of said elastomer part.

4. Valve block for selection of different measuring modules of an analyzing apparatus with at least two valves according to claim 3, wherein said valves are located in a joint valve housing, and said branch lines of said at least two valves depart from a common main line and are connected to said measuring modules of said analyzing apparatus via fittings provided at said valve block.

5. Valve block for selection of different measuring modules of an analyzing apparatus with at least two valves according to claim 1, wherein said valves are located in a joint valve housing, and said branch lines of said at least two valves depart from a common main line and are connected to said measuring modules of said analyzing apparatus via fittings provided at said valve block.

6. Valve block according to claim 5, wherein said valve housing is provided with an upper part holding said elastomer parts, said main lines and said branch lines, and a lower part holding said valve lifters.

7. Valve block according to claim 6, wherein said lower part is provided with a valve drive.

8. Valve block according to claim 6, wherein said upper part is of plexiglass material and said lower part is of aluminum material.

9. Valve block according to claim 8, wherein said lower part of said valve housing is maintained at a constant temperature.

10. Valve block according to claim 5, wherein said valve block is provided with a heat exchanger allocated to said main line for the heating of sample and operating media.

\* \* \* \* \*